US00PP28065P2

(12) United States Plant Patent
Berry

(10) Patent No.: US PP28,065 P2
(45) Date of Patent: May 30, 2017

(54) ***LAGERSTROEMIA* PLANT NAMED '1LI'**

(50) Latin Name: *Lagerstroemia indica*
Varietal Denomination: 1LI

(71) Applicant: Capstone Plants Inc., Grand Saline, TX (US)

(72) Inventor: James B Berry, Edgewood, TX (US)

(73) Assignee: CAPSTONE PLANTS INC., Grand Saline, TX (US)

( * ) Notice: Subject to any disclaimer, the term of this patent is extended or adjusted under 35 U.S.C. 154(b) by 72 days.

(21) Appl. No.: 14/756,352

(22) Filed: Sep. 1, 2015

(51) Int. Cl.
*A01H 5/02* (2006.01)

(52) U.S. Cl.
USPC ..... Plt./252

(58) Field of Classification Search
USPC ..... Plt./252
See application file for complete search history.

(56) References Cited

PUBLICATIONS

UPOV hit on *Lagerstroemia* plant named '#1Li', QZ PBR 20161279, published Oct. 15, 2016.*

* cited by examiner

*Primary Examiner* — Anne Grunberg
(74) *Attorney, Agent, or Firm* — Penny J. Aguirre

(57) ABSTRACT

A new cultivar of *Lagerstroemia indica* plant named '1LI' that is characterized by its very upright plant habit, its foliage that is dark with pink tones in color, its flowers that are vivid coral pink in color, its very vigorous growth habit, its panicles that are long, wide and airy, and its resistance to powdery mildew and leaf spot.

2 Drawing Sheets

Botanical classification: *Lagerstroemia indica.*
Variety denomination: '1LI'.

BACKGROUND OF THE INVENTION

The present invention relates to a new and distinct cultivar of *Lagerstroemia indica*. The new *Lagerstroemia* will hereafter be referred to by its cultivar name, '1LI'. '1LI' is a new cultivar of crape myrtle grown for use as an ornamental landscape plant.

The new cultivar of *Lagerstroemia* is the result of a controlled breeding program conducted by the Inventor in Grande Saline, Tex. The objective of the breeding program is the develop new cultivars of crape myrtle that are pathogen resistant, have dark red pigmented foliage, have unique flower color, and that possess desirable production traits.

'1LI' originated as a seedling that arose from seeds sown from open pollination of *Lagerstroemia indica* 'Best Red' (not patented) as the female parent in September of 2012. '1LI' was selected as a single unique plant in July of 2013 from amongst the resulting seedlings.

Asexual propagation of the new cultivar was first accomplished by the Inventor using semi mature softwood stem cuttings in August of 2013 in Grand Saline, Tex. Asexual propagation by semi mature softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '1LI' as a unique cultivar of *Lagerstroemia.*

1. '1LI' exhibits a very upright plant habit.
2. '1LI' exhibits foliage that is dark brown in color with pink tones.
3. '1LI' exhibits flowers that are vivid coral pink in color.
4. '1LI' exhibits a very vigorous growth habit.
5. '1LI' exhibits panicles that are long, wide and airy.
6. '1LI' exhibits resistance to powdery mildew and leaf spot.

The female parent of '1LI', *Lagerstroemia indica* 'Best Red' differs from '1LI' in having flowers that are deep red in color and in having foliage that is very dark to almost black in color. '1LI' can also be compared to the cultivars 'Caddo' (not patented) and 'Whit III' (U.S. Plant Pat. No. 10,319). 'Caddo' is similar to '1LI' in having a similar flower color. 'Caddo' differs from '1LI' in having a low spreading growth habit, in having a light brown satin-like bark and in having all green foliage. 'Whit III' is similar to '1LI' in having a similar flower color and mildew resistance. 'Whit III' differs from '1LI' in having foliage that is green at times, has less resistance to leaf spot, and in having panicles that are less open and airy.

BRIEF DESCRIPTION OF THE DRAWINGS

The accompanying colored photographs illustrate the overall appearance and distinct characteristics of the new *Lagerstroemia*. The photographs were taken of a plant one year in age (from a rooted cutting) as grown outdoors in one-gallon containers in Grand Saline, Tex.

The photograph in FIG. 1 provides a side view of '1LI' in bloom.

Figure 1:
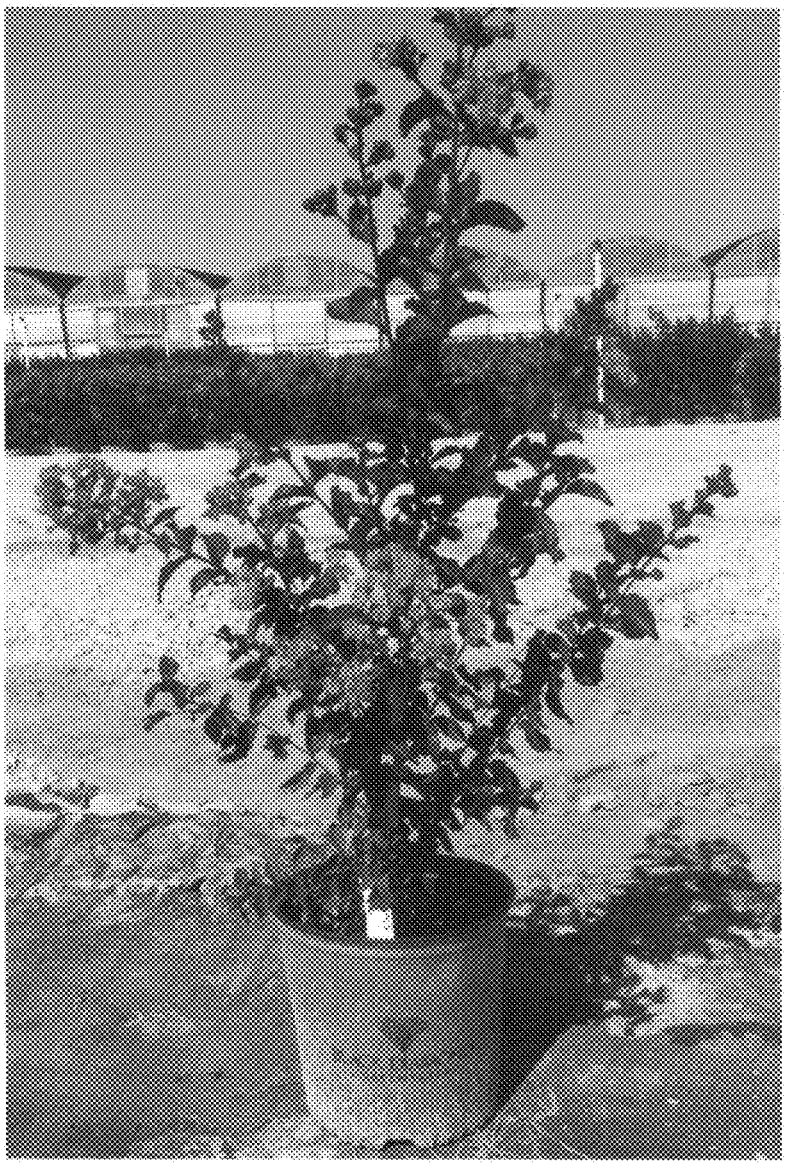
Figure 2:
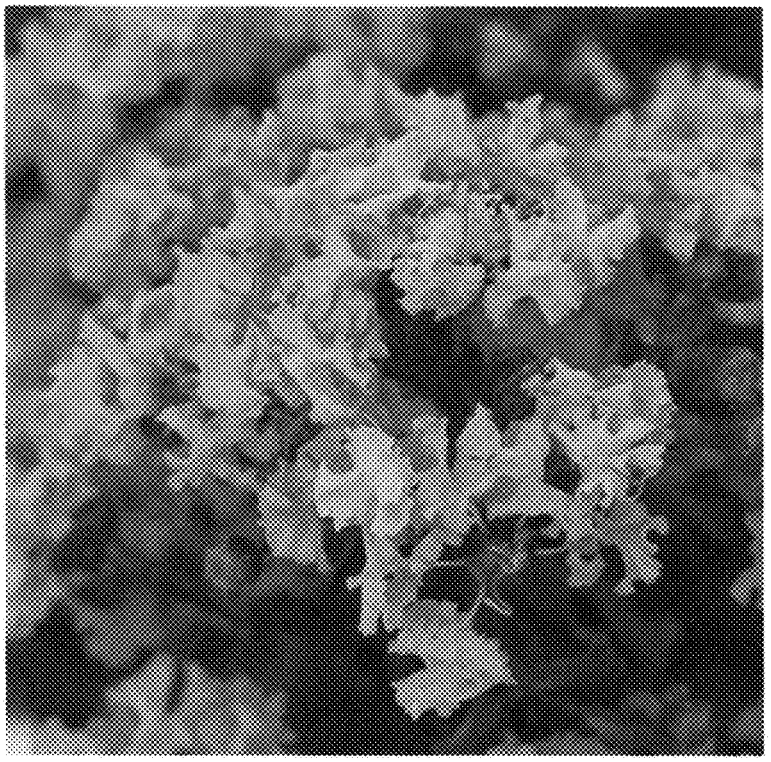

The photograph in FIG. 2 provides a close-up view of an inflorescence of '1LI'.

Figure 3:
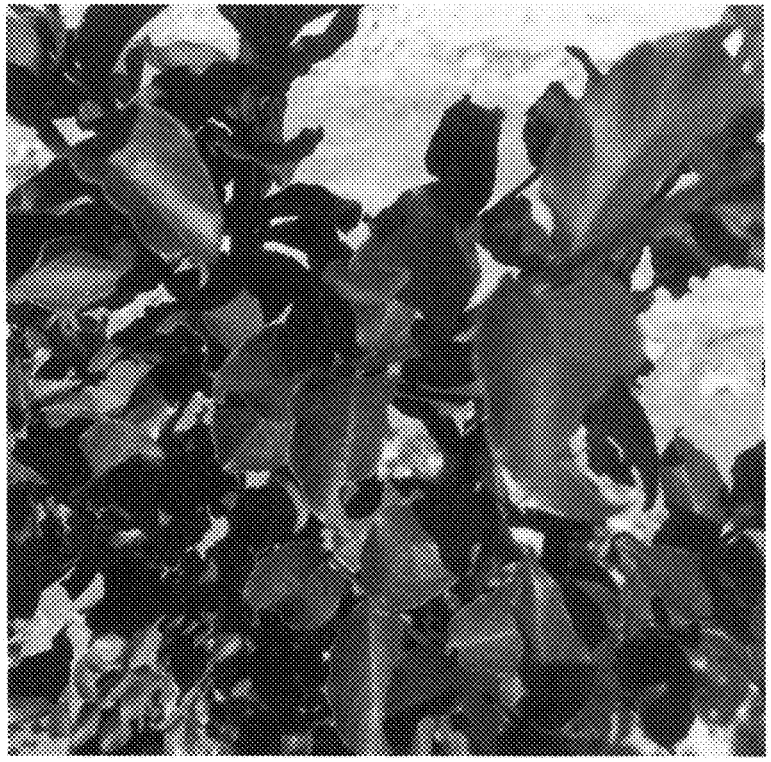

The photograph in FIG. 3 provides a close-up view of the foliage '1LI'.

The colors in the photographs are as close as possible with the digital photography techniques available, the color values cited in the detailed botanical description accurately describe the colors of the new *Lagerstroemia*

DETAILED BOTANICAL DESCRIPTION

The following is a detailed description of plants one year in age (from a rooted cutting) as grown outdoors in one-gallon containers in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Mid June to mid October in Texas.

*Plant type*.—Deciduous shrub.

*Plant habit*.—Upright.

*Height and spread*.—3.7 to 4.3 m in height and an average of 3.7 m in width as grown in the landscape.

*Hardiness*.—At least to U.S.D.A. Zone 6.

*Diseases and pests*.—Resistance to powdery mildew (*Erysiphe lagerstoemia*) and leaf spot (*Cercospora lythracearum*) has been observed.

*Root description*.—Fibrous and fine, 201A in color.

*Root development*.—An average of 2 weeks for root initiation and about 5 weeks to produce a young rooted plant

*Propagation*.—Semi mature softwood stem cuttings.

*Growth rate*.—Very vigorous.

Stem description:

*Shape*.—Young stems; quadrangular with very small wings, mature stems; rounded.

*Stem color*.—Young and mature stems; a blend between 185A and 187B with translucent wings, older stems; a blend between 161A, 164A, 165A, and 200A.

*Stem size*.—Main stems; an average of 43 cm in length (after pruning) and 6 mm in diameter, secondary stems; an average of 30 cm in length and 5 mm in width.

*Stem surface*.—Young and mature stems; glossy, smooth and rubbery, older stems; bark-like, dull, and rugose.

*Stem strength*.—Main stems; strong, secondary stems; moderately strong and flexible.

*Branching*.—Moderately branched, an average of 6 main branches and 9 lateral branches per main branch.

*Internode size*.—An average of 2 cm.

*Stem fragrance*.—Musty fragrance typical for *Lagerstroemia* detected when touched.

Foliage description:

*Leaf shape*.—Elliptic to oval.

*Leaf division*.—Simple.

*Leaf base*.—Rounded.

*Leaf apex*.—Acute to acuminate.

*Leaf venation*.—Pinnate, color; upper surface; mid-rib 183A and slightly covered with minute hairs <0.5 mm in length and close to NN155C in color, lower surface; mid-rib 159A from the base to the center, matches leaf color from the center to the apex; lateral veins upper and lower surface; match leaf color.

*Leaf margins*.—Entire, undulate, slightly covered with minute hairs <0.5 mm in length, close to NN155C in color.

*Leaf arrangement*.—Opposite.

*Leaf attachment*.—Petiolate.

*Leaf surface*.—Upper surface; glossy and leathery and lower surface; moderately glossy and leathery.

*Leaf size*.—An average of 6 cm in length and 3 cm in width.

*Leaf quantity*.—An average of 22 (11 pairs) per main stem and an average of 18 (9 pairs) per lateral stem.

*Leaf color*.—Young and mature upper surface; a blend between 182A and N200A, young and mature lower surface; a blend between 200A and 144A.

*Leaf fragrance*.—Musty fragrance typical for Lagerstroemia detected when touched.

*Petioles*.—An average of 1 mm in length and width, upper and lower surfaces; a blend of N186C and 197A in color and glabrous.

Flower description:

*Inflorescence type*.—Terminal panicle.

*Lastingness of inflorescence*.—About one to two weeks.

*Inflorescence size*.—An average of 14 cm in height and 9 cm in width.

*Inflorescence number*.—An average of 1 per lateral stem.

*Flower number*.—An average of 15 flowers per inflorescence.

*Flower fragrance*.—Mild sweet scent.

*Flower buds*.—Flattened globular shape, an average of 5 mm in diameter and depth, surface; glossy and striate with 6 main grooves protruding from the surface with apical points, color; 183A at the apex fading to 184B at the center and 144B at the base.

*Flower aspect*.—Upright to outwards.

*Flower type*.—Rotate.

*Flower size*.—An average of 3 cm in diameter and 1.7 cm in depth.

*Petals*.—An average of 6, ovate in shape, very curly with sinuate crenate margins, stalked base (attached between sepals), rounded apex, glabrous and dull upper and lower surface, an average of 1.4 cm in length and 1.2 cm in width (stalk portion is about 5 mm in length and <1 mm in width), color; upper and lower surfaces when opening and when fully open; 63B with stalk 63C, petal color does not fade.

*Calyx*.—Campanulate in shape, an average of 8 mm in length and 1 cm in diameter.

*Sepals*.—An average of 6, fused at the base with acute to apiculate apex spreading outwards, elliptic in shape, entire margins, both surfaces glabrous and dull, an average of 8 mm in length and 3 mm in width, with free apex portion 3 mm in length and width, color; outer and inner surfaces when opening and when fully open 183A to 183B.

*Peduncles*.—Moderately strong, an average of 3 cm in length and 2 mm in width, flattened, N79B in color, surface; glossy and rubbery with translucent wings, held at an average angle of 30° to the lateral branch.

*Pedicels*.—Moderately strong, an average of 7 mm in length and 1 mm in width, color; 183A to 183B with 144B near flower attachment, held vertical from peduncle.

Reproductive organs:

*Stamens*.—An average of 30 clustered at the center and 6 evenly distributed around the outside, central stamens; anther; an average of 1 mm in length, dorsifixed, oblong to round in shape, 12A in color, filament; an average of 4 mm in length and 155B in color, outer stamens; anther; an average of 1.5 mm in length, dorsifixed, oblong in shape, 197A to 197C in color, filament; an average of 7 mm in length and 63C to 63D in color, pollen is moderate in quantity and 12C in color.

*Pistils*.—An average of 1, an average of 1.6 cm in length, style; an average of 1.4 cm in length and 182A in color, stigma is club-shaped, an average of 1.5 mm in length and 147A in color, ovary is globose in shape, an average of 2.5 mm in diameter and 157C in color.

*Seed and fruit*.—None observed to date.

It is claimed:

1. A new and distinct cultivar of *Lagerstroemia* plant named '1LI' as herein illustrated and described.

* * * * *